(12) United States Patent
Iida et al.

(10) Patent No.: US 10,094,750 B2
(45) Date of Patent: Oct. 9, 2018

(54) ISOSTATIC BREAKING STRENGTH TESTER AND ISOSTATIC BREAKING STRENGTH TEST METHOD

(71) Applicant: NGK INSULATORS, LTD., Nagoya (JP)

(72) Inventors: Kazuki Iida, Nagoya (JP); Yasumasa Fujioka, Nagoya (JP); Hisazumi Shaku, Nagoya (JP); Kazunari Akita, Nagoya (JP); Yoshihiro Sato, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 15/299,925

(22) Filed: Oct. 21, 2016

(65) Prior Publication Data

US 2017/0153169 A1    Jun. 1, 2017

(30) Foreign Application Priority Data

Nov. 27, 2015   (JP) ................. 2015-232042

(51) Int. Cl.
| | |
|---|---|
| *G01N 3/06* | (2006.01) |
| *G01N 3/10* | (2006.01) |
| *G01N 33/38* | (2006.01) |
| *G01N 3/12* | (2006.01) |

(52) U.S. Cl.
CPC ............. *G01N 3/068* (2013.01); *G01N 3/10* (2013.01); *G01N 3/12* (2013.01); *G01N 33/388* (2013.01);
(Continued)

(58) Field of Classification Search
CPC ............ G01N 3/068; G01N 3/10; G01N 3/12; G01N 33/388; G01N 2203/0067;
(Continued)

(56) References Cited

U.S. PATENT DOCUMENTS 3,906,782 A * 9/1975 Early ................ G01N 3/10
 73/816
5,226,310 A * 7/1993 Steiger ................ E21B 49/006
 73/38
(Continued)

FOREIGN PATENT DOCUMENTS

| JP | 2001-041867 A1 | 2/2001 |
| JP | 2001-242054 A1 | 9/2001 |
| JP | 2010-121966 A1 | 6/2010 |

OTHER PUBLICATIONS

Extended European Search Report (Application No. 16198646.8) dated Apr. 4, 2017.

*Primary Examiner* — Lisa Caputo
*Assistant Examiner* — Nathaniel T Woodward
(74) *Attorney, Agent, or Firm* — Burr & Brown, PLLC (57) ABSTRACT

A breaking strength tester includes: a tubular pressure container having opened both ends to house a part of a pillar-shaped honeycomb structure including a partition walls and a circumferential wall; a tubular pressurization elastic body disposed to surround an entire circumference of a pressurized portion having a length equal to or less than ½ of a length in an axial direction of the circumferential wall; a partial pressurization unit which elastically deforms the pressurization elastic body and applies uniform pressure to the entire circumference of the circumferential wall of the pressurized portion of the honeycomb structure housed in the pressure container up to pressure test strength; and a pressure measurement unit which measures a value of the uniform pressure applied to the circumferential wall by the pressurization elastic body.

12 Claims, 7 Drawing Sheets

(52) U.S. Cl.
CPC ............... *G01N 2203/0067* (2013.01); *G01N 2203/0266* (2013.01); *G01N 2203/0274* (2013.01); *G01N 2203/0647* (2013.01)

(58) Field of Classification Search
CPC ... G01N 2203/0266; G01N 2203/0274; G01N 2203/0647
USPC .......................................................... 73/821
See application file for complete search history.

(56) References Cited

U.S. PATENT DOCUMENTS

| | | | | |
|---|---|---|---|---|
| 5,339,693 | A * | 8/1994 | Rowlands | G01N 3/12 73/49.5 |
| 5,379,645 | A * | 1/1995 | Smart | G01N 3/10 73/794 |
| 5,415,828 | A * | 5/1995 | Watanabe | B28B 3/003 264/109 |
| 5,828,942 | A * | 10/1998 | Tsutsumi | B22F 3/04 419/38 |
| 6,405,602 | B1 * | 6/2002 | Itou | G01N 3/10 73/790 |
| 7,883,599 | B2 * | 2/2011 | Fujita | B28B 1/002 156/285 |
| 8,728,607 | B2 * | 5/2014 | Okazaki | B01D 46/2462 427/397.7 |
| 2002/0157454 | A1 | 10/2002 | Shimada et al. | |
| 2004/0007077 | A1 * | 1/2004 | Hijikata | G01N 3/303 73/799 |
| 2004/0079167 | A1 * | 4/2004 | Boyko | G01N 3/10 73/825 |
| 2009/0188326 | A1 * | 7/2009 | Toyoshima | C04B 35/195 73/788 |
| 2014/0154146 | A1 | 6/2014 | Aoki | |
| 2015/0101397 | A1 | 4/2015 | Poiate Junior et al. | |

* cited by examiner

ISOSTATIC BREAKING STRENGTH TESTER AND ISOSTATIC BREAKING STRENGTH TEST METHOD

"The present application is an application based on JP-2015-232042 filed on Nov. 27, 2015 with Japan Patent Office, the entire contents of which are incorporated herein by reference."

BACKGROUND OF THE INVENTION

Field of the Invention

The present invention relates to an isostatic breaking strength tester and an isostatic breaking strength test method. To be more specific, the invention relates to an isostatic breaking strength tester and an isostatic breaking strength test method that pressurize a part of a ceramic honeycomb structure up to pressure test strength and enable a total inspection of isostatic breaking strength in a process of manufacturing the ceramic honeycomb structure.

Description of the Related Art

Conventionally, measurement has been performed regarding isostatic breaking strength (hereinafter, referred to simply as the "breaking strength") which indicates strength against isotropic external pressure of a ceramic honeycomb structure (hereinafter, referred to simply as the "honeycomb structure") which includes partition walls defining a plurality of cells extending from one end face and the other end face and a circumferential wall provided around the partition walls. The breaking strength is measured to guarantee whether the honeycomb structure has sufficient strength for practical use when it is used in various applications such as a filter member and a heat exchange member, and the breaking strength is employed as one of quality determination criteria to ship the honeycomb structure as a product with breaking strength (a pressure test strength or a guarantee strength) equal to or greater than a reference value.

The breaking strength of the honeycomb structure is measured mainly on the basis of a breaking strength test method stipulated in car standard (JASO M505-87) issued by the Society of Automotive Engineers of Japan. The breaking strength test method is described in detail. A honeycomb structure is clamped with aluminum plates to cover the both end faces, and further wrapped with elastic material such as rubber around a circumferential wall. The honeycomb structure is then submerged and set in a pressure container (a submersion isostatic breaking strength tester) filled with water, and subject to isotropic pressure as water pressure inside the container gradually increases. As the water pressure inside the container gradually increases, the pressure is applied from the periphery of the submerged honeycomb structure, and eventually, a breakage occurs on the partition wall or the circumferential wall of the honeycomb structure. A value of pressure at which the breakage occurs (breaking strength) is measured.

In the above-described breaking strength test method, the preparation before setting the honeycomb structure inside the pressure container is complicated, and those operations take a lot of time in some cases. In addition, since the honeycomb structure is submerged inside the container and is subjected to the pressurization until it breaks, it is difficult for the honeycomb structure used for the measurement to be shipped as a product. Thus, inspections are usually carried out by visually observing the external appearance of the honeycomb structure and the above-described breaking strength test is carried out if it is necessary. Therefore, it is difficult to perform a total inspection of the breaking strength in the process of manufacturing the honeycomb structure.

Meanwhile, the inventors of the present application or the like have been already proposed a compression tester in which a honeycomb structure is pressurized up to predetermined pressure test strength, maintained at the pressure test strength for a certain period of time, and then inspected whether a breakage occurs on a partition wall or a circumferential wall of the honeycomb structure. Accordingly, it is unnecessary to pressurize the honeycomb structure until it breaks, and thus it is possible to perform a total inspection of the breaking strength in a process of manufacturing the honeycomb structure.

Examples of the above-described compression tester have been proposed such as a tester having a configuration in which "a compression test of a measurement sample is performed by arranging an elastic sleeve around an outer circumferential surface of a ceramic measurement sample (corresponding to the honeycomb structure), installing the sample inside a tubular container with an elastic sheet interposed between the elastic sleeve and the tubular container, and injecting a hydrostatic-pressure pressurization medium between the tubular container and the elastic sheet to pressurize" (see Patent Document 1). Another tester have been proposed in which a configuration of "using rubbery material such that an elastic sheet has a thickness of equal to or less than 5 mm and a hardness of 30 to 50 degree" is further added to the compression tester of Patent Document 1 (see Patent Document 2).

Further, a "strength inspection method and a strength inspection device of a honeycomb structure", which are capable of easily and suitably inspecting whether the honeycomb structure satisfies a predetermined guarantee strength, have been proposed (see Patent Document 3). According to the strength inspection method and the strength inspection device, there are two or more peaks of inspection pressure distribution in an axial direction on an outer surface of a skin layer of the honeycomb structure, and inspection pressure is loaded on the honeycomb structure such that each inspection capability of valley portions of the peaks becomes equal to or greater than a guarantee strength (guarantee pressure).

The compression tester, the strength inspection device, and the like described above can keep the pressurization up to a predetermined pressure test strength (guarantee strength), and thus, it is possible to perform the total inspection of the honeycomb structure in any case. Further, it is unnecessary to submerge the honeycomb structure inside the container of the pressure container as in the related art, thus it is possible to simplify the preparation and operations before measurement.

[Patent Document 1] JP-A-2001-41867
[Patent Document 2] JP-A-2001-242054
[Patent Document 3] JP-A-2010-121966

SUMMARY OF THE INVENTION

However, there are problems listed as follows in the measurement of the breaking strength of the honeycomb structure using the above-described compression tester. That is, the compression tester described in Patent Document 1 or 2 has the structure in which the honeycomb structure is pressurized by pressing the elastic sleeve against the entire circumference of the circumferential wall of the honeycomb structure with an elastic sheet interposed therebetween. Thus, it is necessary to apply uniform pressure to the entire outer circumferential surface of the honeycomb structure, and measurement time for one honeycomb structure tends to still increase.

In addition, time is also required for conveying the honeycomb structure to a predetermined position of the compression tester and moving the honeycomb structure from a measurement position after completion of the measurement. As a result, it takes about 10 seconds for the above-described cycle to measure the breaking strength of one honeycomb structure. Thus in a total inspection, the measurement process of the pressure test strength becomes a bottleneck causing retention or the like of a lot of the honeycomb structures waiting for measurement, results in a possibility of decreasing the production efficiency of the honeycomb structure.

Further, in the above-described compression tester or the conventional breaking strength test method according to the car standard, the breakage of the honeycomb structure is often detected based on detection of breaking sound generated when the partition wall is broken or detection of pressure change (pressure drop) during the pressurization. However, there is a risk of missing the breaking sound due to the operating sound of the compression tester or the surrounding noise, thus prompt and accurate detection of the partition wall breakage is difficult in many cases.

On the other hand, in the detection of pressure change, it is sufficiently possible to detect the breakage of the honeycomb structure when a rapid pressure change is detected. However, it is difficult to detect the breakage accurately when the breakage of the partition wall or the like slowly progresses causing a gradual pressure change. Thus, there has been a demand for a method which is capable of accurately detecting the breakage of the honeycomb structure other than or together with the breakage detection methods by the breaking sound or the pressure change.

In addition, "strength inspection method and the strength inspection device" illustrated in Patent Document 3 require to load the inspection pressure so that a peak of the inspection pressure distribution in the axial direction becomes two or more, which makes the strength inspection device complicated as well as makes the inspection complicated since the pressure in the valley portion between the peaks has to be measured.

Thus, the present invention has been made in view of the above-described circumstances, and an object thereof is to provide an isostatic breaking strength tester and an isostatic breaking strength test method which enable a total inspection of breaking strength of a honeycomb structure while preventing a decrease of production efficiency of the honeycomb structure without requiring complicated work at the time of measurement of the breaking strength and are capable of accurately detecting a breakage in a circumferential wall or a partition wall of the honeycomb structure generated by pressurization.

According to the present invention, there are provided an isostatic breaking strength tester (hereinafter, referred to simply as the "breaking strength tester"), and an isostatic breaking strength test method (hereinafter, referred to simply as the "breaking strength test method") in which the above-described problems are solved.

According to a first aspect of the present invention, an isostatic breaking strength tester is provided comprising: a tubular pressure container in which a part of a pillar-shaped ceramic honeycomb structure including lattice-shaped partition walls to define a plurality of cells extending from one end face to another end face and a circumferential wall is housed, the tubular pressure container having at least a part of both ends being opened; a tubular pressurization elastic body disposed inside the pressure container so as to surround an entire circumference of a pressurized portion having a length equal to or less than ½ of a length in an axial direction of the circumferential wall of the ceramic honeycomb structure; a partial pressurization unit for elastically deforming the pressurization elastic body toward the circumferential wall and applying uniform pressure to the entire circumference of the circumferential wall of the pressurized portion of the ceramic honeycomb structure housed in the pressure container up to a pressure test strength; and a pressure measurement unit for measuring a value of the uniform pressure applied to the circumferential wall by the pressurization elastic body.

According to a second aspect of the present invention, the breaking strength tester according to the above-described first aspect is provided, further comprising a breakage pressure determination unit for detecting a pressure drop equal to or greater than a reference value of the pressure during pressurization and determining the pressure drop as occurrence of a breakage in the ceramic honeycomb structure.

According to a third aspect of the present invention, the breaking strength tester according to the above-described first or second aspects is provided, further including: a photographing unit for photographing at least one broken piece of the partition wall and the circumferential wall, the broken piece falling from the ceramic honeycomb structure when a breakage occurs in the ceramic honeycomb structure; and an breakage image determination unit for determining that the breakage occurs in the ceramic honeycomb structure when the broken piece is detected from the photographed image photographed by the photographing unit.

According to a fourth aspect of the present invention, the breaking strength tester according to the above-described first or second aspects is provided, wherein the pressure container is provided with a container bottom portion that supports the ceramic honeycomb structure from below, the breaking strength tester further including: a photographing unit for photographing the container bottom portion of the pressure container from above after the ceramic honeycomb structure pressurized up to the pressure test strength by the partial pressurization unit is conveyed from the pressure container; and a breakage image determination unit for determining that a breakage occurs in the ceramic honeycomb structure when at least one broken piece of the partition wall and the circumferential wall of the ceramic honeycomb structure is detected from the photographed image photographed by the photographing unit.

According to a fifth aspect of the present invention, the breaking strength tester according to any one of the above-described first to fourth aspects is provided, wherein the partial pressurization unit includes a position of the circumferential wall clamped from both sides to support by a clamping device being used to convey the ceramic honeycomb structure to the pressure container, and a region including any one side of the one end face and the other end face of the ceramic honeycomb structure in the pressurized portion.

According to a sixth aspect of the present invention, the breaking strength tester according to any one of the above-described first to fifth aspects is provided, wherein the pressurization elastic body is elastically deformed using any one of water and air.

According to a seventh aspect of the present invention breaking strength test method is provided including: a ceramic honeycomb structure housing process of housing a part of a pillar-shaped ceramic honeycomb structure including lattice-shaped partition walls to define a plurality of cells extending from one end face to another end face and a circumferential wall in a tubular pressure container, the tubular pressure container having at least a part of both ends being opened; a partial pressurization process of elastically deforming a tubular pressurization elastic body disposed inside the pressure container so as to surround an entire circumference of a pressurized portion having a length equal to or less than ½ of a length in an axial direction of the circumferential wall of the ceramic honeycomb structure, and applying a uniform pressure to the entire circumference of the circumferential wall of the pressurized portion of the ceramic honeycomb structure housed in the pressure container up to pressure test strength; and a pressure measurement process of measuring a value of the uniform pressure applied to the circumferential wall by the pressurization elastic body.

According to an eighth aspect of the present invention, the breaking strength test method according to the above-described seventh aspect is provided, further including a breakage pressure determination process of detecting a pressure drop equal to or greater than a reference value of the pressure during pressurization and determining the pressure drop as occurrence of a breakage in the ceramic honeycomb structure.

According to a ninth aspect of the present invention, the breaking strength test method according to the above-described seventh or eighth aspects is provided, further including: a photographing process of photographing at least one broken piece of the partition wall and the circumferential wall, the broken piece falling from the ceramic honeycomb structure when a breakage occurs in the ceramic honeycomb structure; and a breakage image determination process of determining that the breakage occurs in the ceramic honeycomb structure when the broken piece is detected from the photographed image photographed in the photographing process.

According to a tenth aspect of the present invention, the breaking strength test method according to the above-described seventh or eighth aspects is provided, wherein the pressure container is provided with a container bottom portion that supports the ceramic honeycomb structure from below, the breaking strength test method further including: a photographing process of photographing the container bottom portion of the pressure container from above after the ceramic honeycomb structure pressurized up to the pressure test strength in the partial pressurization process is conveyed from the pressure container; and a breakage image determination process of determining that a breakage occurs in the ceramic honeycomb structure when at least one broken piece of the partition wall and the circumferential wall of the ceramic honeycomb structure is detected from the photographed image photographed in the photographing process.

According to an eleventh aspect of the present invention, the breaking strength test method according to any one of the above-described seventh to tenth aspects is provided, further including a ceramic honeycomb structure inversion process of inverting upper and lower positions of the one end face and the other end face of the ceramic honeycomb structure, wherein each value of the pressure on the one end face side and the other end face side of the ceramic honeycomb structure is measured.

According to a twelfth aspect of the present invention, the breaking strength test method according to any one of the above-described seventh to eleventh aspects is provided, further including: a submersion breakage process of introducing the ceramic honeycomb structure which is not broken at the predetermined pressure test strength into a submersion isostatic breaking strength tester, and applying water pressure to the ceramic honeycomb structure being completely submerged to break the ceramic honeycomb structure; a submersion breaking strength measurement process of measuring a value of a submersion breaking strength at a point in time when the ceramic honeycomb structure is broken; and a target test strength calculation process of calculating a target test strength in the partial pressurization process based on correlation between the measured submersion breaking strength value and a value of the pressure test strength pressurized in the partial pressurization process.

According to the breaking strength tester and the breaking strength test method of the present invention, it is possible to significantly reduce measurement time of the breaking strength by applying pressure to a part of the circumferential wall of the honeycomb structure (equal to or less than ½ of the length in the axial direction) up to the pressure test strength using the pressurization elastic body. As a result, it is possible to perform a total inspection for the breaking strength of the honeycomb structure, and there is no risk of reducing productive efficiency of the honeycomb structure.

Further, it is possible to detect the breakage of the honeycomb structure based on the pressure change by detecting the pressure drop equal to or greater than the predetermined reference value and to detect and determine the breakage of the honeycomb structure by detecting the broken piece of the circumferential wall or the partition wall, generated by the breakage of the honeycomb structure, based on the photographed image.

DESCRIPTION OF THE PREFERRED EMBODIMENTS

Hereinafter, embodiments of a breaking strength tester (isostatic breaking strength tester) and a breaking strength test method (isostatic breaking strength test method) will be described with reference to the drawings. Incidentally, the breaking strength tester and the breaking strength test method of the present invention are not particularly limited to the following embodiments, and various types of alteration, correction and improvement in design can be added as long as not departing from a gist of the present invention.

(1) Breaking Strength Tester of First Embodiment

Figure 1:
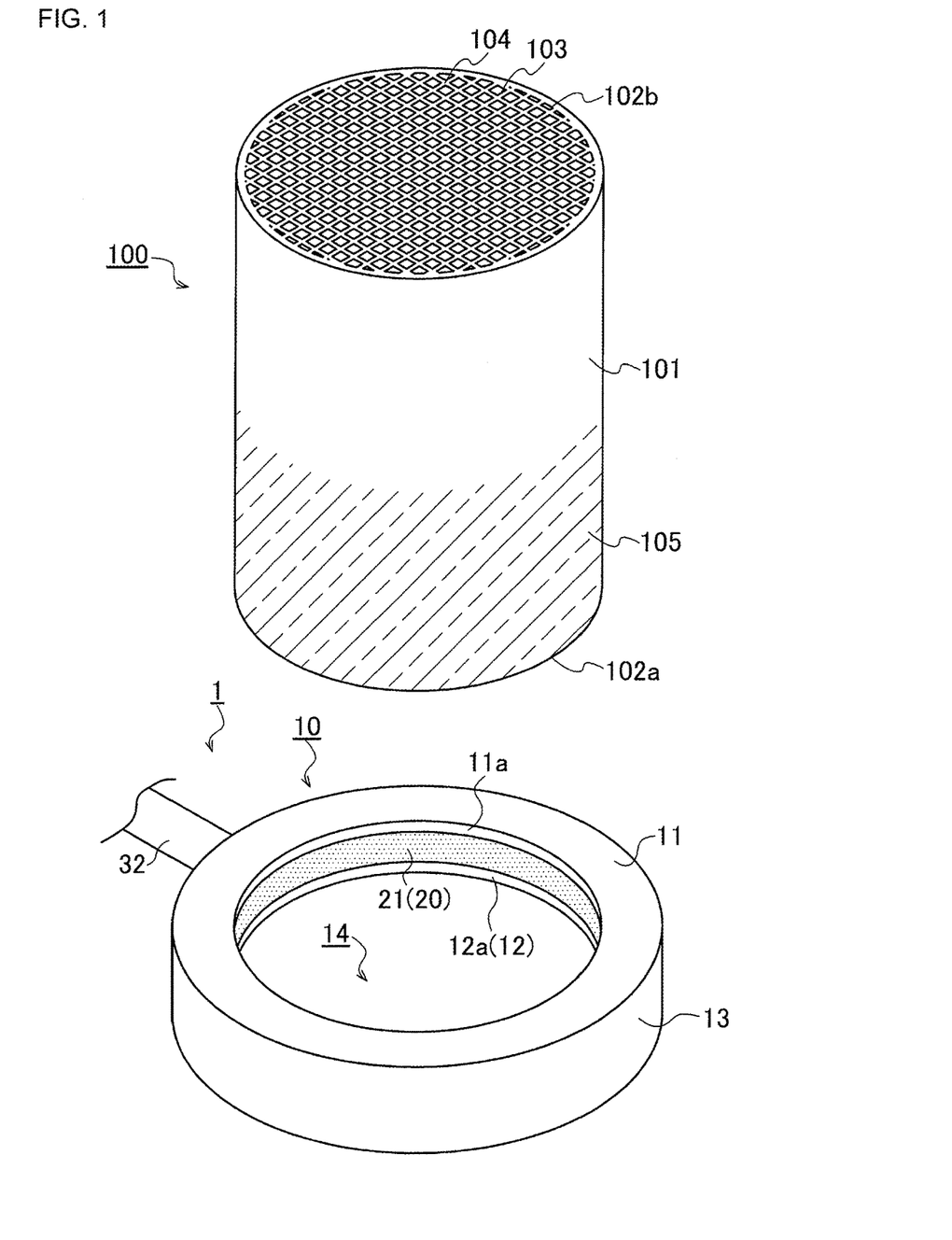
FIG. 1 is a perspective view schematically showing a schematic configuration of a pressure container and a honeycomb structure as a measurement target of a breaking strength of a breaking strength tester according to a first embodiment.
Figure 2:
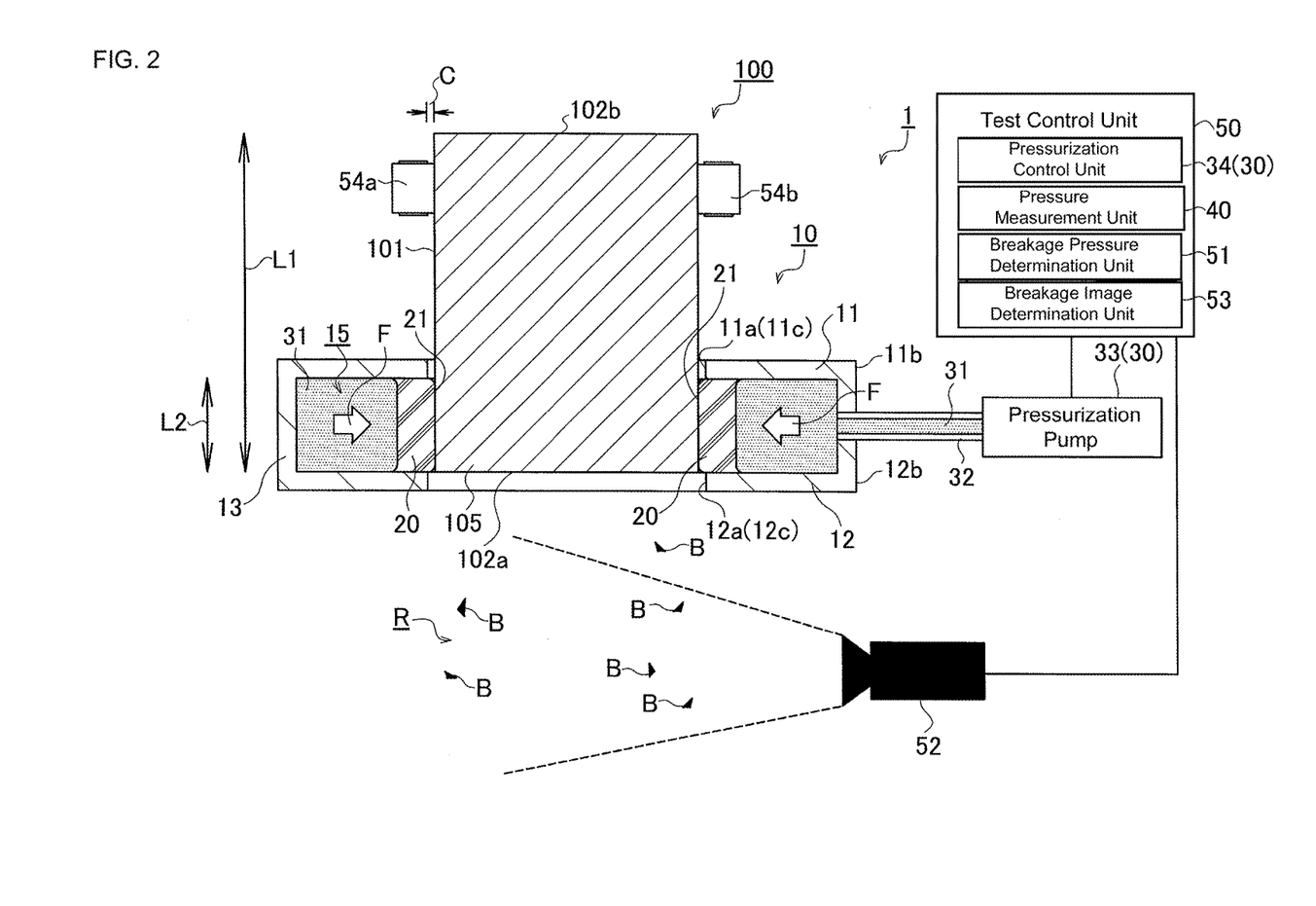
FIG. 2 is an explanatory diagram schematically showing a schematic configuration and a functional configuration of the breaking strength tester according to the first embodiment and an example of detection of a broken piece on the basis of a photographed image.
Figure 3:
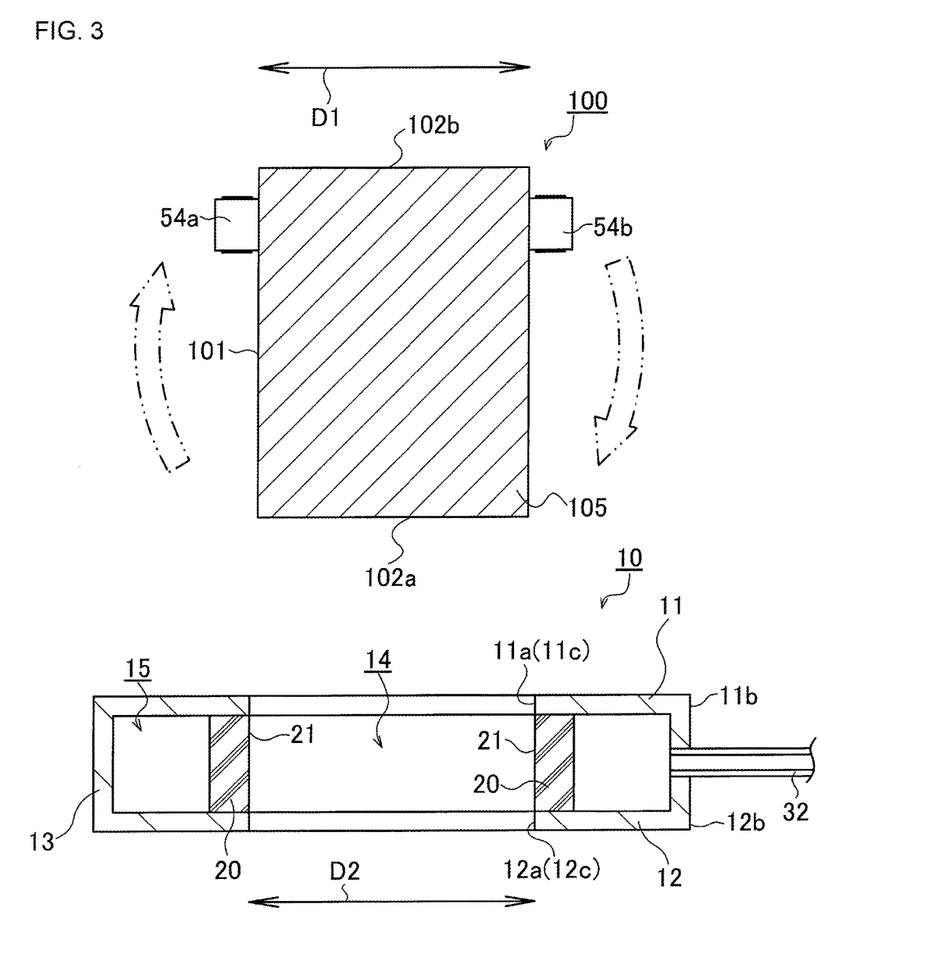
FIG. 3 is an explanatory diagram schematically showing an example in which one end face and the other end face of the honeycomb structure are vertically inverted.

As shown mainly in FIGS. 1 to 3, a breaking strength tester 1 according to a first embodiment of the present invention is mainly provided with: a cylindrical pressure container 10 which is capable of housing a part of a round pillar-shaped honeycomb structure 100 whose breaking strength is a target of measurement and has both opened ends; a pressurization elastic body 20 disposed inside the pressure container 10 so as to surround entire circumference of a pressurized portion 105 having a length L2 equal to or less than ½ of a length L1 (see FIG. 2 regarding the respective lengths) in an axial direction of a circumferential wall 101 of the honeycomb structure 100; a partial pressurization unit 30 which elastically deforms the pressurization elastic body 20 toward the circumferential wall 101 of the honeycomb structure 100 and applies uniform pressure to the pressurized portion 105 of the honeycomb structure 100 housed in a container interior space 14 (to be described later in detail) of the pressure container 10 over the entire circumference of the circumferential wall 101 up to a pressure test strength; and a pressure measurement unit 40 which measures a value of the uniform pressure applied to the circumferential wall 101 by the pressurization elastic body 20.

Further, to be specific, the honeycomb structure 100 whose breaking strength is measured by the breaking strength tester 1 of the first embodiment is mainly configured to include a quadrangular lattice-shaped partition walls 104 that defines each of a plurality of cells 103 extending from one end face 102a (corresponding to a lower side in FIG. 2) to another end face 102b (corresponding to an upper side in FIG. 2), each end face having a circular shape, and the circumferential wall 101 provided around the partition walls 104, and the honeycomb structure has substantially a round pillar-shaped form and structure as a whole. Further, the above-described pressurized portion 105 is set by a width of the length L2 equal to or less than ½ of the length L1 in the axial direction of the circumferential wall 101. Incidentally, both the partition walls 104 and the circumferential wall 101 forming the honeycomb structure 100 are formed using a material containing ceramic as a main component. Incidentally, a cross section of the honeycomb structure 100 is shown by hatching and details of a cell 103 and the partition walls 104 are not shown in FIG. 2 to simplify the illustration (similarly shown in FIGS. 3 and 4).

The pressure container 10 forming the breaking strength tester 1 applies isotropic external pressure partially to the pressurized portion 105 on the circumferential wall 101 either on the one end face 102a side or the other end face 102b side of the honeycomb structure 100, and the pressure container 10 is configured to include an annular (donut-shaped) container upper portion 11 having a top open end 11a opened upward, an annular container bottom portion 12 having substantially the same shape as the container upper portion 11 and having a bottom open end 12a which spaced apart from the container upper portion 11 and opened downward at a position opposing the top open end 11a, and a cylindrical-shaped container cylindrical portion 13 connecting respective outer peripheral edges 11b and 12b of the container upper portion 11 and the container bottom portion 12.

Each size of an opening diameter of the top open end 11a of the container upper portion 11 and an opening diameter D2 (to be described later in detail) of the pressurization elastic body 20 is formed to be slightly greater than a honeycomb diameter D1 (see FIG. 3) of the circular one end face 102a (or the other end face 102b) which is perpendicular to the axial direction (corresponding to the vertical direction in FIG. 2) of the honeycomb structure 100. Thus, it is possible to insert the honeycomb structure 100 from the top open end 11a by moving the honeycomb structure 100 having the one end face 102a directed downward from a top of the pressure container 10.

A part of the honeycomb structure 100 (herein, the one end face 102a side, see FIG. 2) is housed in the container interior space 14 of the inner side of the pressure container 10 in the state of maintaining a predetermined clearance C from the opening diameter of the top open end 11a. Incidentally, the opening diameter of the bottom open end 12a of the container bottom portion 12 is not particularly limited, and may be the same as the opening diameter of the top open end 11a or different from the opening diameter of the top open end 11a.

Meanwhile, the pressurization elastic body 20 forms a cylindrical shape and is disposed to face the container interior space 14 on the inner side of the pressure container 10 so as to connect respective inner peripheral edges 11c and 12c of the top open end 11a and the bottom open end 12a. Thus, a top end and a bottom end of the pressurization elastic body 20 are open. In addition, the opening diameter D2 of the cylindrical pressurization elastic body 20 and the opening diameter of the top open end 11a of the pressure container 10 are substantially coincide with each other in the breaking strength tester 1 of the first embodiment.

Therefore, the predetermined clearance C is formed between the elastic body surface 21 of the pressurization elastic body 20 and the pressurized portion 105 (the circumferential wall 101) and the respective surfaces of the elastic body surface 21 and the pressurized portion 105 are in parallel with each other in a state in which the pressurized portion 105 of the honeycomb structure 100 is housed in the pressure container 10. The pressurization elastic body 20 is made of a rubber material, which is elastically deformable depending on stress, and has a hardness of 30 to 50 degree for example.

The elastic body surface 21 of the pressurization elastic body 20 is elastically deformed by expansion to contact with the pressurized portion 105 of the honeycomb structure 100 through uniform pressure, whereby the honeycomb structure 100 can be pressurized. Herein, the pressurization elastic body 20 and the pressure container 10 are adhered such that the joining portion has a watertight structure. Accordingly, the pressurization space 15, which is surrounded by the container upper portion 11, the container bottom portion 12, and the container cylindrical portion 13 of the pressure container 10 and the pressurization elastic body 20, is formed as a hermetically sealed space to prevent leakage of a pressurization medium 31 (water, air or the like) from the pressurization space 15.

Meanwhile, a partial pressurization unit 30 is configured to introduce the pressurization medium 31 into the pressurization space 15 to expand the pressurization elastic body 20 disposed in the pressure container 10 toward a pressurization direction F which is directed to the container interior space 14. That is, the pressurization makes it possible to elastically deform the elastic body surface 21 of the pressurization elastic body 20, which is positioned to be substantially coincide the inner peripheral edges 11c and 12c of the top open end 11a and the bottom open end 12a of the pressure container 10 in a non-pressurization state (for example, see FIG. 3), toward the container interior space 14.

As shown in FIG. 2, the part of the honeycomb structure 100 on the one end face 102a side is inserted into the pressure container 10 and is set in the housed state. Thus, isotropically uniform pressure can be applied to the entire circumference of the pressurized portion 105 by strongly pressing the elastic body surface 21 against the pressurized portion 105 of the honeycomb structure 100 through the expansion of the pressurization elastic body 20.

The partial pressurization unit 30 for expanding the pressurization elastic body 20 is provided with an medium introduction tube 32 communicating with the pressurization space 15 of the pressure container 10 to introduce the pressurization medium 31 into the pressurization space 15, a pressurization pump 33 to feed the pressurization medium 31 into the pressurization space 15 through the medium introduction tube 32 to change the pressure of the pressurization space 15, and a pressurization control unit 34 serving as a functional configuration to control pressurization by the pressurization pump 33.

It is possible to increase the pressure inside the pressurization space 15 to be higher than the atmospheric pressure using the pressurization medium 31 fed to the pressurization space 15 by controlling the pressurization pump 33 with the pressurization control unit 34. As a result, the pressurization elastic body 20 can be expanded toward the container interior space 14. Incidentally, the breaking strength tester 1 of the first embodiment exemplifies that the pressurization elastic body 20 is elastically deformed by water pressure using "water" as the pressurization medium 31. Incidentally, in the breaking strength tester of the present invention, the pressurization medium 31 is not limited to water, and various gases such as air or liquids other than water can be suitably used.

Meanwhile, a pressure measurement unit 40 is configured to measure a uniform pressure value applied to the pressurized portion 105 of the honeycomb structure 100 pressurized by the partial pressurization unit 30, and for example, may be a unit that measures the pressure inside the pressurization space 15 by receiving a sensor signal from a known pressure measurement sensor (not shown) installed in the pressurization space 15 or the medium introduction tube 32, or a unit that measures the pressure value based on value measured by a pressure gauge (not shown) installed in the pressurization pump 33 of the partial pressurization unit 30. The pressure value is measured at a predetermined time interval (for example, an interval of $1/100$ s) to be linked with a breakage pressure determination unit 51 described later, whereby a real time measurement of a pressure value change can be achieved. Further, the pressure values bring pressure distribution having one peak along the axial length L1 of the honeycomb structure 100.

Further, the breaking strength tester 1 of the first embodiment is provided with a breakage pressure determination unit 51, a photographing unit 52 and a breakage image determination unit 53 as other configurations and functional configurations. The breakage pressure determination unit 51 detects a pressure drop equal to or greater than a predetermined reference value based on the pressure values measured by the pressure measurement unit 40 during the pressurization, and when the breakage pressure determination unit detects the pressure drop, detects a breakage of the honeycomb structure 100 and determines that the breakage occurred. The photographing unit 52 photographs a broken piece B of at least one of the partition walls 104 and the circumferential wall 101 falling from the honeycomb structure 100 through the bottom open end 12a when the breakage occurs in the honeycomb structure 100 during the pressurization. The lower side of the bottom open end 12a of the pressure container 10 is set to be a photographing region R. The breakage image determination unit 53 analyzes an image photographed by the photographing unit 52, and when the broken piece B is detected in the photographed image, detects the breakage of the honeycomb structure 100 and determines that the breakage occurred. Incidentally, each of the pressurization control unit 34 as a part of the partial pressurization unit 30, the pressure measurement unit 40, the breakage pressure determination unit 51, and the breakage image determination unit 53 is stored in a test control unit 50 which is configured to perform various types of control and analysis.

The test control unit 50 can use, for example, a function of a commercially available personal computer, and can exhibit various functions by installing various types of software. Meanwhile, the photographing unit 52 connected to the test control unit 50 can use, for example, a known CCD camera and the like, and is capable of capturing a moving image with respect to the specified photographing region R when the honeycomb structure 100 is pressurized.

Incidentally, the image photographed by the photographing unit 52 is sent to a storage medium (not shown) such as an HDD of the test control unit 50, and can be archived and stored. Thus a real time detection as well as a follow-up detection of the broken piece B can be achieved based on the photographed image to verify presence or absence of the breakage of the honeycomb structure 100.

Further, the breaking strength tester 1 of the first embodiment is controlled to be inter-connected with a conveyance mechanism (not shown) that conveys the honeycomb structure 100 sent from the previous step to the vicinity of the pressure container 10, sets a part of the honeycomb structure 100 to be housed in the pressure container 10 in a state in which the breaking strength thereof is measurable, and after the measurement from the pressure container 10, takes out the honeycomb structure 100 and sends the honeycomb structure 100 to the subsequent step.

The conveyance mechanism is provided with a pair of chucks 54a and 54b that clamp the circumferential wall 101 of the honeycomb structure 100 from both sides and can execute various motions such as movement of the honeycomb structure 100 in the vertical direction, the horizontal direction, and vertical inversion (to be described later in detail), and the chunks 54a and 54b can convey the honeycomb structure 100 to a desired position. Herein, the chucks 54a and 54b correspond to clamping devices according to the present invention.

(2) Breaking Strength Test Method

The breaking strength test method is implemented for the honeycomb structure 100 using the above-described breaking strength tester 1. First, the honeycomb structure 100 serving as a measurement target for the breaking strength test is housed in the pressure container 10 using the chucks 54a and 54b (the ceramic honeycomb structure housing process). To be specific, the vicinity of the upper side (the other end face 102b side) of the honeycomb structure 100 is clamped from both the sides of the circumferential wall 101 by the pair of chucks 54a and 54b, and the honeycomb structure is conveyed to above the top open end 11a of the pressure container 10 with the clamped state. Thereafter, the one end face 102a of the honeycomb structure 100 is inserted into the top open end 11a from above.

The opening diameter of the top open end 11a and the opening diameter D2 of the pressurization elastic body 20 connected to the inner peripheral edge 11c of the top open end 11a are formed to be slightly greater than the honeycomb diameter D1 of the honeycomb structure 100. Thus, a part of the honeycomb structure 100 is promptly housed in the container interior space 14 of the pressure container 10 by the motion of inserting the one end face 102a of the honeycomb structure 100 into the top open end 11a. At this time, each length of the pressure container 10 and the pressurization elastic body 20 in the axial direction is defined such that the part housed in the pressure container 10 (the pressurized portion 105) has the axial length L2 equal to or less than ½ of the axial length L1 of the honeycomb structure 100. Accordingly, the expending part of the pressurization elastic body 20 can be shortened compared to that of the related art by defining the length of the pressurization elastic body 20 to be in contact with the circumferential wall 101 of the honeycomb structure 100 within the above-described range. As a result, the pressurization elastic body 20 allows prompt expansion and contraction, which achieves a stable pressurization against the circumferential wall 101, as well as a shortening of time required for pressurization.

The pressurization control unit 34 of the test control unit 50 is controlled with the honeycomb structure in a housed state in the pressure container 10 to operate the pressurization pump 33 and feed the pressurization medium 31 into the pressurization space 15 of the pressure container 10. As a result, the pressurization space 15 is filled with the pressurization medium 31 introduced through the medium introduction tube 32, and the internal pressure gradually increases. As the internal pressure of the pressurization space 15 becomes higher than the atmospheric pressure, the pressurization elastic body 20, which partitions the pressurization space 15 and the container interior space 14, elastically deforms and expands toward the container interior space 14. The uniform pressure is partially applied to the pressurized portion 105 of the honeycomb structure 100 having the part housed in the pressure container 10 over the entire circumference of the pressurized portion 105 (a partial pressurization process).

At this time, the pressure toward the honeycomb structure 100 pressurized by the pressurization pump is controlled up to predetermined pressure test strength. Further, the time required for each step of starting the pressurization, maintaining the pressure test strength, and restoring to the atmospheric pressure is defined in advance. The breaking strength tester 1 of the first embodiment can significantly reduce the time required from the start of pressurization up to the pressure test strength as compared to that of the existing compression tester, and shorten the breaking strength measurement time since only the length L2, which is equal to or less than ½ of the axial length L1 of the honeycomb structure 100, is pressurized up to the pressure test strength. To be more specific, the introduction amount of the pressurization medium 31 such as water introduced into the pressurization space 15 to elastically deform the pressurization elastic body 20 is reduced, whereby the pressurization time of the honeycomb structure 100 can be reduced. In addition, by defining the length L2 to be equal to or less than ½ of the length L1 in the axial direction, it is possible to use the honeycomb structures which have the same cross-sectional shape but only the axial lengths L1 (honeycomb length) are different. That is, it is unnecessary to replace the pressure container 10 of the breaking strength tester 1. As a result, the breaking strength tester 1 of the first embodiment has an advantage of reducing time which is required for various settings to measure breaking strength of a plurality of different types of honeycomb structures. A specific example of reduction in time of the measurement of the breaking strength is given. The breaking strength tester 1 of the first embodiment takes about two seconds for one-time pressurization and allows to measure breaking strength of the two honeycomb structures 100 for about five seconds in single inspection tact. In contrast, an existing compressor requires about 10 seconds for one-time pressurization, thus requires 15 seconds to measure breaking strength of the two honeycomb structures in single inspection tact.

Figure 6:
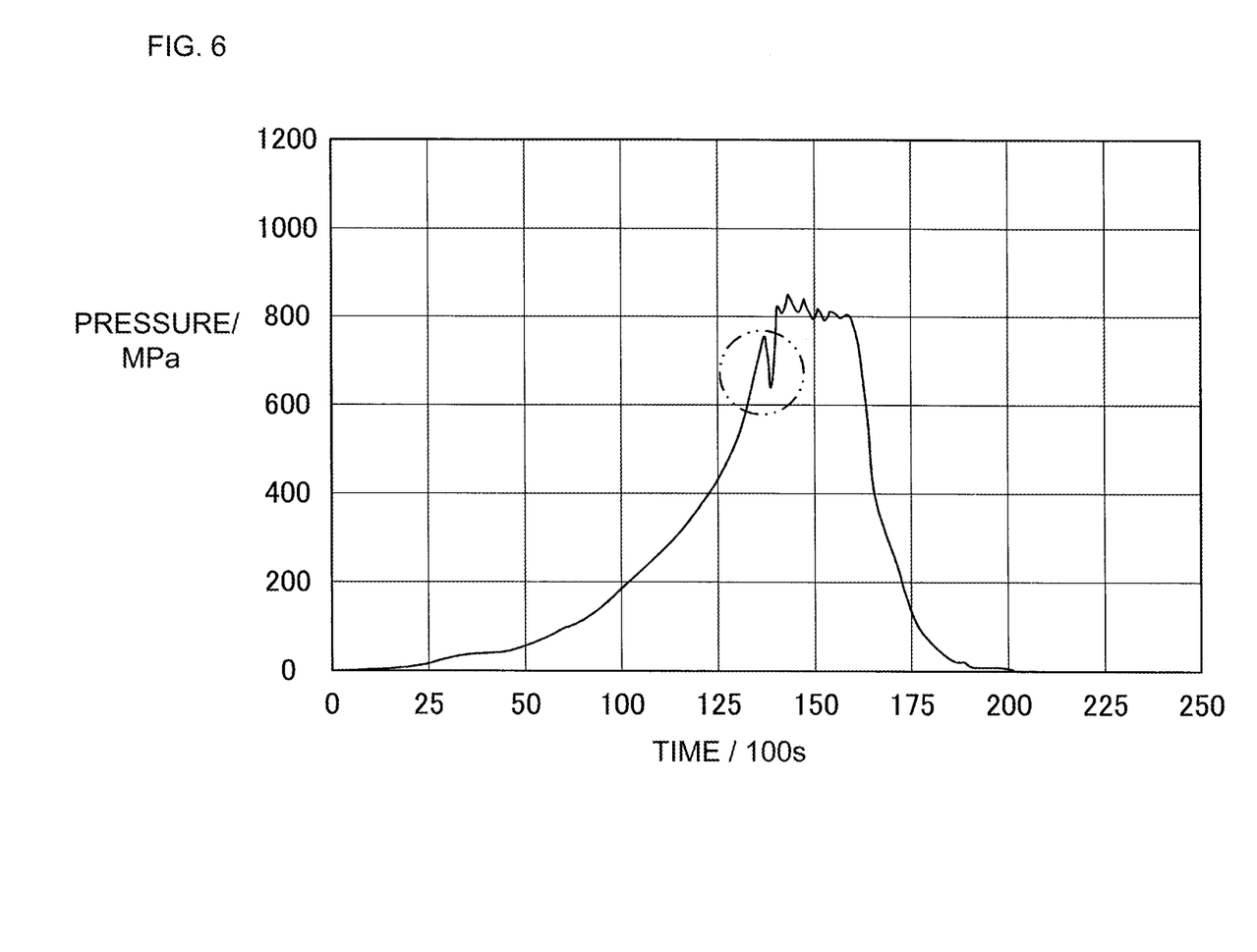
FIG. 6 is a graph showing relation between elapse of time from start of pressurization and pressure which shows an example of detection of breakage of the honeycomb structure using detection of pressure drop.

In the partial pressurization process, a value of the pressure applied to the honeycomb structure 100 is measured at the predetermined time interval (for example, the interval of 1/100 s) in real time (a pressure measurement process). At this time, when a pressure drop of the measured pressure value equal to or greater than the predetermined reference value is detected, the breakage pressure determination unit 51 determines that a breakage occurs in the partition wall 104 or the circumferential wall 101 of the honeycomb structure 100 (a breakage pressure determination process). Herein, the pressure drop equal to or greater than the reference value is set by a case where a pressure drop equal to or greater than, for example, 100 kPa is detected per unit time or the like (see inside the two-dot chain line circle in FIG. 6). Incidentally, when the pressure drop is detected through the breakage pressure determination process, the pressurization control unit 34 is controlled and the supply of the pressurization medium 31 through the pressurization pump 33 is stopped.

The breaking strength test method of the first embodiment further includes photographing the lower side of the pressure container 10 as the photographing region R during the partial pressurization process (a photographing process). When the breakage occurs in the partition wall 104 or the circumferential wall 101 corresponding to the length L2 of the pressurized portion 105 of the honeycomb structure 100 during the pressurization, a broken piece B falls from the honeycomb structure 100 due to a breakage and passes through the photographing region R through the bottom open end 12a of the container bottom portion 12 of the pressure container 10. The photographing unit can capture the broken piece B in a photographed image. The photographed image is sent from the photographing unit 52 to the breakage image determination unit 53 of the test control unit 50 in real time, and analysis thereof is performed using a known image analysis processing technique. As a result, when the broken piece B is detected in the photographed image, it is determined that the breakage occurs in the honeycomb structure 100 (a breakage image determination process).

That is, the breaking strength tester 1 of the first embodiment can detect the breakage of the honeycomb structure 100 not only by the detection of the pressure change based on the rapid pressure drop, but also by the detection of broken piece B in the photographed image. Thus, even when it is difficult to detect the breakage of the honeycomb structure 100 only through the conventional detection of the pressure change based on the pressure drop, it is possible to reliably detect the breakage of the honeycomb structure 100 through combination with detection of the breakage using the photographed image. This prevents the inappropriate honeycomb structure 100 which does not satisfy a product quality criterion from being sent to the subsequent step, particularly in the total inspection. In the case of the breaking strength tester 1 of the first embodiment, the broken piece B falling from the honeycomb structure 100 due to the breakage does not remain in the pressure container 10. Thus, it is unnecessary to perform removal and clean-up operation of the broken piece B as in the related art.

Meanwhile, when it is determined that the breakage does not occur in the honeycomb structure 100 in any of the breakage pressure determination process and the breakage image determination process even after being pressurized up to the pressure test strength and held for a predetermined time at the pressure test strength, the honeycomb structure 100 is once lifted up above the pressure container 10 in the state of being clamped by the pair of chucks 54a and 54b and thereafter, upper and lower positions of the honeycomb structure 100 are inverted (a ceramic honeycomb structure inversion process, see the two-dot chain line arrow in FIG. 3). That is, the one end face 102a side after the breaking strength measurement is inverted from the lower position to the upper position. In this state, the other end face 102b side is inserted from the top open end 11a to be housed in the pressure container 10. Thereafter, the respective steps according to the above-described partial pressurization process are repeated to measure a breaking strength of the other end face 102b side. Accordingly, the breaking strength is measured twice by changing measurement points with respect to the single honeycomb structure 100.

In each breaking strength measurement, it is configured that the clamped position definitely receives pressurization by the pressurization elastic body 20 even when the upper and lower positions clamped by the pair of chucks 54a and 54b are inverted. That is, the above-described clamped position is included in the pressurized portion 105. This allows confirmation that even the portion clamped by the pair of chucks 54a and 54b and received a predetermined chucking pressure has a strength equal to or greater than the pressure test strength.

As described above, it is possible to perform the total inspection regarding the breaking strength of the honeycomb structure 100 during the manufacturing process according to the breaking strength tester 1 of the first embodiment and the breaking strength test method. In particular, more reliable detection can be achieved regarding the defective honeycomb structure 100 with strength poverty and the like in the internal partition wall 104 compared to the conventional external appearance inspection by visual observation. Also, it is possible to previously prevent the inappropriate honeycomb structure 100 from being sent to the subsequent step and shipped as a product. Further, limiting the pressurized part by the pressurization elastic body 20 to a part of the honeycomb structure 100 dramatically reduces the measurement time from the start to the end of pressurization compared to the related art, and this eliminates retention of the honeycomb structures 100 waiting for measurement prior to the breaking strength measurement process. As a result, the production efficiency of the honeycomb structure 100 improves.

In addition, it is possible to implement the detection of the breakage with respect to the honeycomb structure 100 in combination with the conventional detection of the pressure change using the pressure drop and the detection of the breakage using the photographed image. As a result, more reliable breakage detection of the honeycomb structure 100 is achieved, and the breakage detection accuracy can be improved.

(3) Breaking Strength Tester of Second Embodiment

Figure 4:
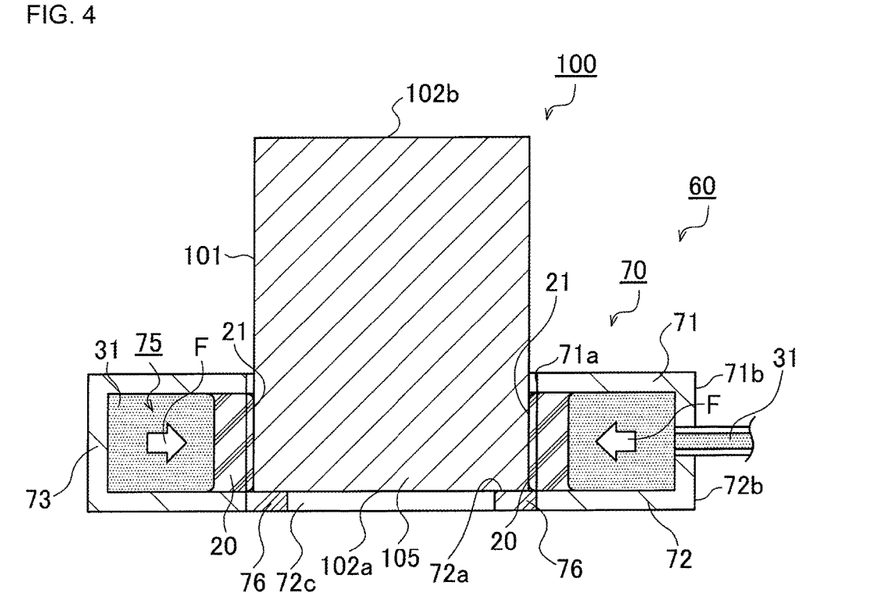
FIG. 4 is an explanatory diagram schematically showing a schematic configuration of a breaking strength tester according to a second embodiment.
Figure 5:
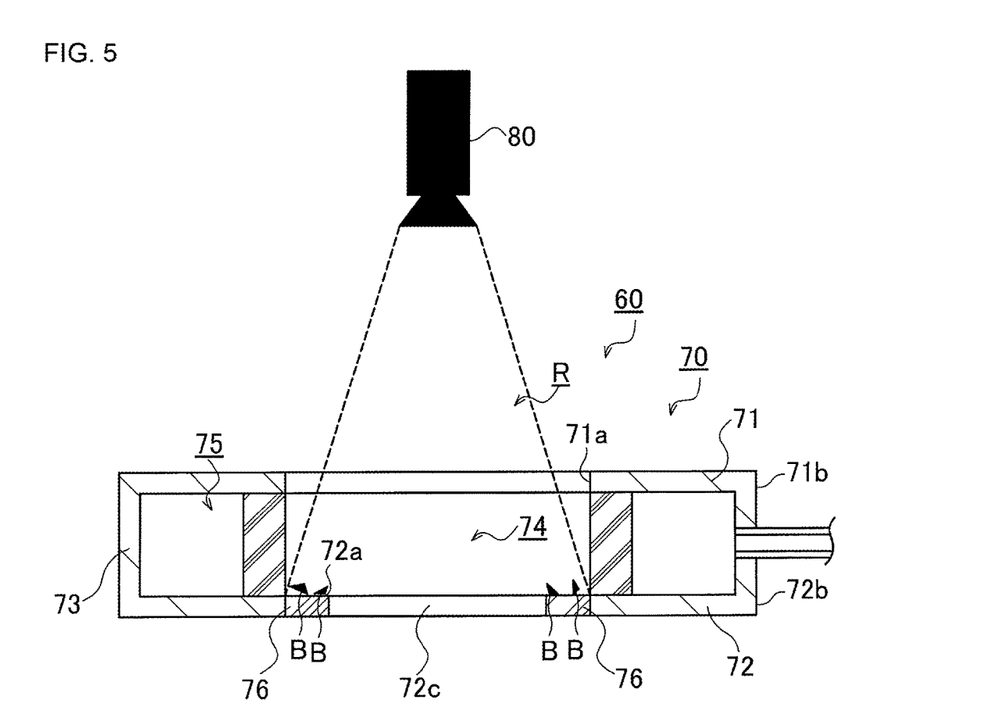
FIG. 5 is an explanatory diagram schematically showing an example of detection of a broken piece on the basis of a photographed image according to the breaking strength tester of the second embodiment.

Next, a breaking strength tester 60 of a second embodiment, which is another exemplary configuration of the present invention, will be described with reference mainly to FIGS. 4 and 5. As shown mainly in FIGS. 4 and 5, a breaking strength tester 60 according to the second embodiment of the present invention is mainly provided with: a cylindrical pressure container 70 which is opened upward and capable of housing a part of a round pillar-shaped honeycomb structure 100 whose breaking strength is a target of measurement and has a bottom open end 72c positioned at the center of a container bottom portion 72 and an outer circumference support portion 76 provided around the bottom open end 72c; a cylindrical pressurization elastic body 20 disposed inside the pressure container 10 so as to surround an entire circumference of a length L2 equal to or less than ½ of a length L1 (see FIG. 2) in an axial direction of a circumferential wall 101 of the honeycomb structure 100; a partial pressurization unit 30 which elastically deforms the pressurization elastic body 20 toward the circumferential wall 101 of the honeycomb structure 100 and applies uniform pressure to a pressurized portion 105, which is a part of the circumferential wall 101 of the honeycomb structure 100 housed in a container interior space 14 of the pressure container 10, over the entire circumference of the pressurized portion 105 up to pressure test strength; and a pressure measurement unit 40 which measures a value of the pressure applied to the pressurized portion 105 by the pressurization elastic body 20. Herein, the same honeycomb structure 100 serving as the measurement target of the breaking strength is used as that of the breaking strength tester 1 of the first embodiment, and the detailed description thereof will be omitted.

The pressure container 70 is configured to include; an annular container upper portion 71 having a top open end 71a opened upward; an outer circumference support portion 76 which is positioned to face to the container upper portion 71 and is capable of supporting the vicinity of an outer circumference of the honeycomb structure 100 from below; a container bottom portion 72 in which the center of a bottom portion of the pressure container 70 is opened; and a cylindrical-shaped container cylindrical portion 73 connecting respective outer peripheral edges 71b and 72b of the container upper portion 71 and the container bottom portion 72. That is, a difference from the pressure container 10 of the breaking strength tester 1 of the first embodiment is that the container bottom portion 72 includes the outer circumference support portion 76 and the bottom open end 72c. Incidentally, the outer circumference support portion 76 includes a cushion member (not shown) such as rubber provided at a contact portion with the honeycomb structure 100 in order to mitigate impact caused by the contact with the vicinity of the outer circumference of the honeycomb structure 100 to be housed therein. The outer circumference support portion 76 provided in the container bottom portion 72 makes it easy for the honeycomb structure 100 to be positioned and housed in the pressure container 70.

Further, since the container bottom portion 72 includes the outer circumference support portion 76 in the breaking strength tester 60 of the second embodiment, it is difficult to detect a broken piece B when a photographing unit 80 is installed at a lower side of the container bottom portion 72, which is a photographing region, as in the breaking strength tester 1 of the first embodiment. Herein, when the honeycomb structure 100 is pressurized, it is known that the broken piece B, which is generated by pressurization, appears mainly from the vicinity of the outer circumference of the honeycomb structure 100. The broken piece B hardly appears at the center of the honeycomb structure 100 due to crack or the like even when the bottom open end 72c is provided at the center of the container bottom portion 72. Thus, the photographing unit 80 is arranged at an upper position of the top open end 71a of the container upper portion 71 of the pressure container 70 so as to be capable of photographing a container interior space 74 from top in the breaking strength tester 60 of the second embodiment (see FIG. 5). That is, the installation position of the photographing unit 80 is different from the photographing unit 52 of the breaking strength tester 1 of the first embodiment.

Other configurations and operational effects of the breaking strength tester 60 of the second embodiment are the same or substantially the same as those of the breaking strength tester 1 of the first embodiment, and thus, the detailed description thereof will be omitted in order to simplify the description. Further, the same configurations as those of the breaking strength tester 1 described above are denoted by the same reference numerals, and the description thereof will be omitted. Further, some configurations such as a test control unit are not illustrated in order to simplify the illustration.

(4) Breaking Strength Test Method Using Breaking Strength Tester of Second Embodiment The breaking strength test method is implemented for the honeycomb structure 100 using the above-described breaking strength tester 60. Incidentally, the honeycomb structure 100 serving as a measurement target for the breaking strength test is housed in the pressure container 70 (a ceramic honeycomb structure housing process). Herein, the ceramic honeycomb structure housing process is the substantially the same as in the case of using the breaking strength tester 1 of the first embodiment described above, and thus, the detailed description thereof will be omitted.

A pressurization control unit (not shown) of the test control unit (not shown) is controlled after the honeycomb structure 100 is housed in the pressure container 70, a pressurization pump (not shown) is operated, and a pressurization medium 31 is introduced into a pressurization space 75 of the pressure container 70. As a result, the pressurization space 15 is filled with the pressurization medium 31 introduced through a medium introduction tube, and the internal pressure thereof gradually increases. As the internal pressure of the pressurization space 75 becomes higher than the atmospheric pressure, the pressurization elastic body 20, which partitions the pressurization space 75 and the container interior space 74, elastically deforms and expands toward the container interior space 74. The uniform pressure is partially applied to the entire circumference of the pressurized portion 105 of the honeycomb structure 100 having the part housed in the pressure container 10 (a partial pressurization process). The details of the partial pressurization process have been described already, and thus, will not be described herein.

When the honeycomb structure 100 is pressurized through the partial pressurization process up to the pressure test strength and determined that there is no breakage in a breakage pressure determination process, the honeycomb structure 100 is once lifted up above the pressure container 70 in a state in which the circumferential wall 101 is clamped between a pair of chucks (not shown), and thereafter, the honeycomb structure is conveyed to a position apart from an upper side of the top open end 71a of the pressure container 70.

Further, a container bottom face 72a (upper face of the outer circumference support portion 76) of the container bottom portion 72 of the pressure container 70 after the honeycomb structure 100 is conveyed from the pressure container 70 is photographed from above using the photographing unit 80 (a photographing process). Herein, a region passing through the top open end 71a of the pressure container 70 to the container bottom face 72a is defined as a photographing region R. When a breakage occurred in a partition wall 104 or the circumferential wall 101 of the honeycomb structure 100 during the pressurization and the broken piece B remains in the container bottom face 72a due to the breakage, the broken piece B can be found on the upper face of the outer circumference support portion 76 around the bottom open end 72c opened at the center in the photographed image. The photographed image is sent from the photographing unit 80 to a breakage image determination unit (not shown) of the test control unit, and analysis is performed using a known image analysis processing technique. As a result, when the broken piece B is detected in the photographed image, it is determined that the breakage occurred in the honeycomb structure 100 (a breakage image determination process).

That is, the breaking strength test method of the second embodiment allows detection of the breakage of the honeycomb structure 100 by a pressure change based on a rapid pressure drop as well as by detecting the broken piece B from the photographed image, which is photographed from the upper side of the pressure container 70. In particular, the broken piece B generated in the vicinity of the outer circumference of the honeycomb structure 100 due to the breakage remains on the upper face of the outer circumference support portion 76 since the outer circumference support portion 76 is provided in the container bottom portion 72 of the pressure container 70, and thus, it is possible to reliably detect the broken piece B using the photographed image. Thus, even when it is difficult to detect the breakage of the honeycomb structure 100 only through the conventional detection of the pressure change based on the pressure drop, it is possible to reliably detect the breakage of the honeycomb structure 100 through combination with detection of the breakage using the photographed image. As a result, the inappropriate honeycomb structure 100 hardly flows to the subsequent step particularly in the case of the total inspection. Incidentally, it is possible to remove and drop the broken piece B on the upper face of the outer circumference support portion 76 through the bottom open end 72c opened at the center after acquiring the photographed image of the broken piece B. As a result, it is possible to promptly remove and clean up the broken piece B. For example, it takes about 80 seconds to remove the broken piece B in the case of the pressure container of the conventional compression tester having a closed container bottom portion, but the breaking strength tester 60 of the second embodiment achieves to reduce the time to about 15 to 20 seconds. In addition, the outer circumference support portion 76 achieves easy positioning of the honeycomb structure 100.

Meanwhile, the honeycomb structure 100, which is pressurized to the pressure test strength and held for a predetermined time at the pressure test strength and determined that no breakage occurred in the honeycomb structure 100 in any of the breakage pressure determination process and the breakage image determination process, upper and lower positions of the honeycomb structure 100 are inverted (a ceramic honeycomb structure inversion process), and one end face 102a side after the breaking strength measurement is inverted from the lower position to the upper position. In this state, the other end face 102b side is inserted from the top open end 71a to be housed in the pressure container 10. Thereafter, the respective steps according to the above-described partial pressurization process are repeated to measure a breaking strength of the other end face 102b side. Accordingly, the breaking strength is measured twice by changing measurement points for the single honeycomb structure 100.

As described above, it is possible to perform the total inspection regarding the breaking strength of the honeycomb structure 100 during the manufacturing process according to the breaking strength tester 60 and the breaking strength test method of the second embodiment. Also, it is possible to previously prevent the inappropriate honeycomb structure 100 from being sent to the subsequent step and shipped as a product similar to the breaking strength tester 1 of the first embodiment. In particular, additional detection of the breakage using the photographed image can be implemented to detect the breakage of the honeycomb structure 100 together with the conventional detection of the pressure change using the pressure drop. As a result, more reliable breakage detection of the honeycomb structure 100 can be achieved.

(5) Calculation of Target Test Strength

The breaking strength test method according to the present invention is capable of calculating target test strength in the partial pressurization process. To be specific, the method further including: a submersion breakage process of extracting one honeycomb structure 100 from honeycomb structures which are pressurized up to the pressure test strength by the breaking strength tester 1 or 60 of the first embodiment or the second embodiment but no breakage was confirmed, introducing the honeycomb structure 100 into a submersion isostatic breaking strength tester (corresponding to the pressure container described in the Background), and applying water pressure to the entirely submerged honeycomb structure 100 until the partition wall 104 or the circumferential wall 101 thereof breaks; a submersion breaking strength measurement process of measuring a value of the submersion breaking strength at a point in time when the breakage occurs in the honeycomb structure 100; and a target test strength calculation process of calculating the target test strength in the partial pressurization process based on correlation between the value of measured submersion breaking strength and the value of the pressure test strength pressurized in the partial pressurization process. Accordingly, the correlation between the submersion breaking strength and the pressure test strength is established, and it is possible to specify the target test strength which is an indication to what extent the honeycomb structure 100 can be pressurized in the total inspection in the breaking strength testers 1 and 60 of the first embodiment and the second embodiment.

Figure 7:
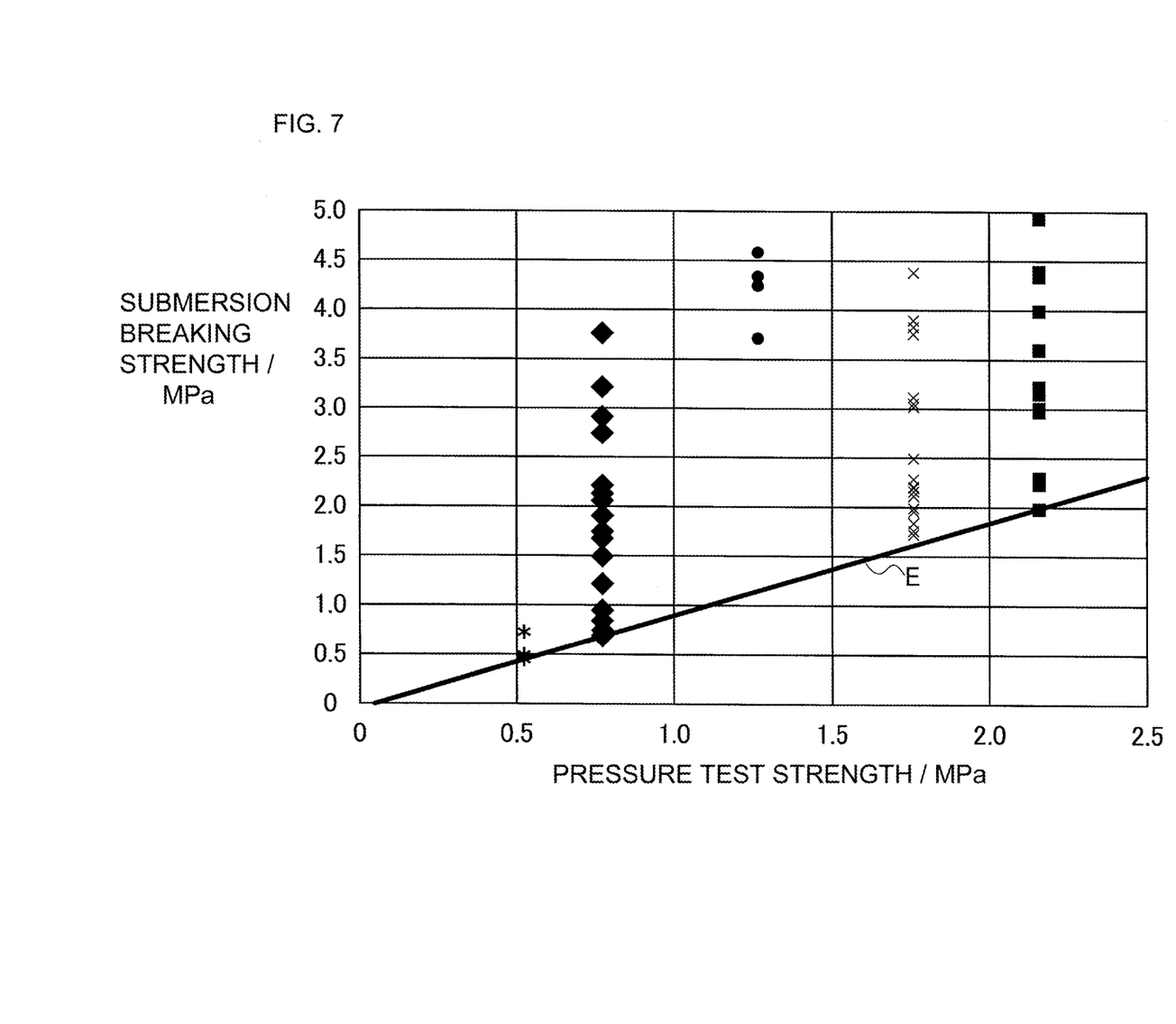
FIG. 7 is a graph showing correlation between pressure test strength and submersion breaking strength.

FIG. 7 is a graph showing correlation between a pressure test strength indicated by the horizontal axis and a submersion breaking strength indicated by the vertical axis. Herein, a linear correlation expression E having a predetermined gradient (see FIG. 7) is obtained by connecting a plurality of plots indicating lowest submersion breaking strengths in the respective pressure test strengths with a straight line. Accordingly, the target test strength can be obtained in accordance with the correlation expression E, and by setting the target test strength as the pressure test strength, the breaking strength testers 1 and 60 of the present invention can be applied in the total inspection of the honeycomb structure 100.

A breaking strength tester and a breaking strength test method of the present invention can be used for measurement of a breaking strength of a honeycomb structure, and particularly, can be suitably used for in-line measurement of a breaking strength during a process of manufacturing the honeycomb structure.

DESCRIPTION OF REFERENCE NUMERALS

1, 60: breaking strength tester (isostatic breaking strength tester), 10 and 70: pressure container, 11 and 71: container upper portion, 11a and 71a: top open end, 11b, 12b, 71b and 72b: outer peripheral edge, 11c and 12c: inner peripheral edge, 12 and 72: container bottom portion, 12a and 72c: bottom open end, 13 and 73: container cylindrical portion, 14 and 74: container interior space, 15 and 75: pressurization space, 20: pressurization elastic body, 21: elastic body surface, 30: partial pressurization unit, 31: pressurization medium, 32: medium introduction tube, 33: pressurization pump, 34 pressurization control unit, 40: pressure measurement unit, 50: test control unit, 51: breakage pressure determination unit, 52 and 80: photographing unit, 53: breakage image determination unit, 54a and 54b: chuck (clamping device), 72a: container bottom face, 76: outer circumference support portion, 100: honeycomb structure, 101: circumferential wall, 102a: one end face, 102b: other end face, 103: cell, 104: partition wall, 105: pressurized portion, B: broken piece, C: clearance, D1: honeycomb diameter, D2: opening diameter, E: correlation expression, F: pressurization direction, L1: length in axial direction, L2: length that is ½ of length in axial direction, R: photographing region

What is claimed is:
1. An isostatic breaking strength tester comprising:
 a tubular pressure container in which a part of a pillar-shaped ceramic honeycomb structure including lattice-shaped partition walls to define a plurality of cells extending from one end face to another end face and a circumferential wall is housed, the tubular pressure container having at least a part of both ends being opened;
 a tubular pressurization elastic body disposed inside the tubular pressure container so as to surround an entire circumference of a pressurized portion of the ceramic honeycomb structure, said pressurized portion having a length equal to or less than ½ of the total axial length of the circumferential wall of the ceramic honeycomb structure;
 a partial pressurization unit for elastically deforming the pressurization elastic body toward the circumferential wall and applying uniform pressure only to the entire circumference of the circumferential wall of the pressurized portion of the ceramic honeycomb structure housed in the tubular pressure container up to a pressure test strength; and
 a pressure measurement unit for measuring a value of the uniform pressure applied to the circumferential wall by the pressurization elastic body.
2. The isostatic breaking strength tester according to claim 1, further comprising
 a breakage pressure determination unit for detecting a pressure drop equal to or greater than a reference value of the pressure during pressurization and determining the pressure drop as occurrence of a breakage in the ceramic honeycomb structure.

3. The isostatic breaking strength tester according to claim 1, further comprising:
a photographing unit for photographing at least one broken piece of the partition wall and the circumferential wall, the broken piece falling from the ceramic honeycomb structure when a breakage occurs in the ceramic honeycomb structure; and
a breakage image determination unit for determining that the breakage occurs in the ceramic honeycomb structure when the broken piece is detected from the photographed image photographed by the photographing unit.

4. The isostatic breaking strength tester according to claim 1, wherein the tubular pressure container is provided with a container bottom portion that supports the ceramic honeycomb structure from below,
the isostatic breaking strength tester further comprising:
a photographing unit for photographing the container bottom portion of the tubular pressure container from above after the ceramic honeycomb structure pressurized up to the pressure test strength by the partial pressurization unit is conveyed from the tubular pressure container; and
a breakage image determination unit for determining that a breakage occurs in the ceramic honeycomb structure when at least one broken piece of the partition wall and the circumferential wall of the ceramic honeycomb structure is detected from the photographed image photographed by the photographing unit.

5. The isostatic breaking strength tester according to claim 1, wherein the partial pressurization unit includes a position of the circumferential wall clamped from both sides for support by a clamping device being used to convey the ceramic honeycomb structure to the tubular pressure container.

6. The isostatic breaking strength tester according to claim 1, wherein
the pressurization elastic body is elastically deformed using any one of water and air.

7. An isostatic breaking strength test method comprising:
a ceramic honeycomb structure housing process of housing a part of a pillar-shaped ceramic honeycomb structure including lattice-shaped partition walls to define a plurality of cells extending from one end face to another end face and a circumferential wall in a tubular pressure container, the tubular pressure container having at least a part of both ends being opened;
a partial pressurization process of elastically deforming a tubular pressurization elastic body disposed inside the tubular pressure container so as to surround an entire circumference of a pressurized portion of the ceramic honeycomb structure, said pressurized portion having a length equal to or less than ½ of the total axial length of the circumferential wall of the ceramic honeycomb structure, and applying uniform pressure only to the entire circumference of the circumferential wall of the pressurized portion of the ceramic honeycomb structure housed in the tubular pressure container up to a pressure test strength; and
a pressure measurement process of measuring a value of the uniform pressure applied to the circumferential wall by the pressurization elastic body.

8. The isostatic breaking strength test method according to claim 7, further comprising
a breakage pressure determination process of detecting a pressure drop equal to or greater than a reference value of the pressure during pressurization and determining the pressure drop as occurrence of a breakage in the ceramic honeycomb structure.

9. The isostatic breaking strength test method according to claim 7, further comprising:
a photographing process of photographing at least one broken piece of the partition wall and the circumferential wall, the broken piece falling from the ceramic honeycomb structure when a breakage occurs in the ceramic honeycomb structure; and
a breakage image determination process of determining that the breakage occurs in the ceramic honeycomb structure when the broken piece is detected from the photographed image photographed in the photographing process.

10. The isostatic breaking strength test method according to claim 7, wherein the tubular pressure container is provided with a container bottom portion that supports the ceramic honeycomb structure from below,
the isostatic breaking strength test method further comprising:
a photographing process of photographing the container bottom portion of the tubular pressure container from above after the ceramic honeycomb structure pressurized up to the pressure test strength in the partial pressurization process is conveyed from the tubular pressure container; and
a breakage image determination process of determining that a breakage occurs in the ceramic honeycomb structure when at least one broken piece of the partition wall and the circumferential wall of the ceramic honeycomb structure is detected from the photographed image photographed in the photographing process.

11. The isostatic breaking strength test method according to claim 7, further comprising
a ceramic honeycomb structure inversion process of inverting upper and lower positions of the one end face and the other end face of the ceramic honeycomb structure,
wherein each value of the pressure on a side of the one end face and a side of the other end face of the ceramic honeycomb structure is measured.

12. The isostatic breaking strength test method according to claim 7, further comprising:
a submersion breakage process of introducing the ceramic honeycomb structure which is not broken at the predetermined pressure test strength into a submersion isostatic breaking strength tester, and applying water pressure to the ceramic honeycomb structure being completely submerged to break the ceramic honeycomb structure;
a submersion breaking strength measurement process of measuring a value of a submersion breaking strength at a point in time when the ceramic honeycomb structure is broken; and
a target test strength calculation process of calculating target test strength in the partial pressurization process based on correlation between the measured value of the submersion breaking strength and a value of the pressure test strength pressurized in the partial pressurization process.

* * * * *